United States Patent [19]

Sandstrom

[11] Patent Number: 5,375,451
[45] Date of Patent: Dec. 27, 1994

[54] TESTING SYSTEM FOR DISSIPATIVE MECHANICAL PHENOMENA

[75] Inventor: Perry W. Sandstrom, Madison, Wis.

[73] Assignee: Wisconsin Alumni Research Foundation, Madison, Wis.

[21] Appl. No.: 991,116

[22] Filed: Dec. 16, 1992

[51] Int. Cl.$^5$ .............................................. G01N 3/56
[52] U.S. Cl. ................................................. 73/7; 73/577
[58] Field of Search ..................................... 73/7–10, 73/86, 104, 54.24–54.27, 54.41, 577–579, 583, 778, 808, 811

[56] References Cited

U.S. PATENT DOCUMENTS

| | | | |
|---|---|---|---|
| 895,980 | 8/1908 | Derihon | 73/7 |
| 2,338,537 | 1/1944 | Podesta | 73/7 |
| 2,573,168 | 10/1951 | Mason et al. | 73/7 X |
| 2,582,223 | 1/1952 | Blackburn et al. | 73/7 |
| 2,990,712 | 7/1961 | Weber | 73/7 |
| 3,069,892 | 12/1962 | Gjertsen | 73/7 |
| 3,554,007 | 1/1971 | Hu | 73/7 |
| 3,710,614 | 1/1973 | Oppliger | 73/54.26 |
| 3,712,117 | 1/1973 | Fitzgerald et al. | 73/54.26 |
| 3,945,241 | 3/1976 | Brown | 73/7 |
| 4,177,434 | 12/1979 | Ida | 73/54.26 X |
| 4,524,610 | 6/1985 | Fitzgerald et al. | 73/54.25 |
| 4,566,181 | 1/1986 | Matusik et al. | 73/54.25 X |
| 4,764,394 | 8/1988 | Conrad | 427/38 |
| 4,788,466 | 11/1988 | Paul et al. | 73/54.41 X |
| 4,864,852 | 9/1989 | Boone | 73/7 X |
| 5,054,313 | 10/1991 | Fitzgerald et al. | 73/54.27 |
| 5,157,962 | 10/1992 | Fitzgerald et al. | 73/54.24 |
| 5,292,596 | 3/1994 | Privett, III et al. | 428/660 |

FOREIGN PATENT DOCUMENTS

| | | | |
|---|---|---|---|
| 1416893 | 8/1988 | U.S.S.R. | 73/7 |
| 1471112 | 4/1989 | U.S.S.R. | 73/7 |

OTHER PUBLICATIONS

*Patent Abstracts of Japan;* "Device for Measuring Surface Characteristics"; Grp P1506, vol. 17, No. 141, ABS pub date (Mar. 23, 1993) (04–315033).
"Mechanism of Fretting Corrosion", H. H. Uhlig, J.App.Mech, 21, Dec., 1954, pp. 401–407.
"Fretting Corrosion of Mild Steel in Air and in Nitrogen", I. M. Feng and H. H. Uhlig, J.App.Mech, 21, Dec., 1954, pp. 395–400.
"The Fretting Corroison of Mild Steel", J. S. Halliday and W. Hirst, Proc. Roy. Soc. London, A–236, Mar., 1956, pp. 411–425 & plates 17–19.
"Testing Machines To Study Fretting Wear", J. Gansheimer and G. Friedrich, Wear, 17, 1971, pp. 407–419.
*Fretting Corrosion,* Chapter 7, R. B. Waterhouse, Pergamon Press, New York, 1972, pp. 106–108.
"Prevention of Fretting by Ion Plated Film", N. Ohmae, T. Nakai and T. Tsukizoe, Wear, 30, 1974, pp. 299–309.
"The Fretting Wear of Mild Steel From 200° to 500° C", P. L. Hurricks, Wear, 30, 1974, pp. 189–212.
"Towards A General Theory of Tribological Systems", H. Czichos and J. Molgaard, Wear, 44, 1977, pp. 247–264.
"An Overview of the Delamination Theory of Wear", N. P. Suh, Wear, 44, 1977, pp. 1–16.
"Apparatus For Studying Fretting Fatique In Vacuum", C. Poon and D. W. Hoeppner, Rev. Sci. Instrum. 50(2), Feb., 1979, pp. 171–176.

(List continued on next page.)

*Primary Examiner*—Tom Noland
*Attorney, Agent, or Firm*—Andrus, Sceales, Starke & Sawall

[57] ABSTRACT

A method and apparatus is provided for testing dissipative mechanical phenomena, including fretting wear. An actuator (54) effects frictional oscillatory slip motion between a stylus (32) and a workpiece (30) in contact. A displacement transducer (62) detects the amplitude of the slip motion, and a control loop (60) responds to the displacement transducer controls the actuator to provide constant amplitude slip motion under changing frictional fretting wear conditions of the workpiece as the workpiece wears during the oscillatory slip motion. The oscillator is driven at its resonant frequency, and the power required to maintain constant amplitude slip motion at resonant frequency is monitored (64).

10 Claims, 5 Drawing Sheets

OTHER PUBLICATIONS

"A New Machine for Studying Surface Damage Due to Wear and Fretting", D. Kusner, C. Poon and D. W. Hoeppner, *Materials Evaluation Under Fretting Conditions,* ASTM STP 760 Jun. 1981, edited by S. R. Brown, Warminster, Pa., pp. 17–29.

"Measurement of the Wear Properties of Metallic Solids With A Falex Lubricant Testing Machine", E. Hale, Rev. Sci. Instrum. 53(8), Aug. 1982, pp. 1255–1260.

"Ion Implantation and Related Treatments Applied in Tribology", G. Dearnaly *Surface Engineering,* edited by R. Kassowsky and S. Singhal (S–Gravenhague, the Netherlands, Martinus Nyhoff, 1984) pp. 125–147.

"Physics of Ion Implantation (Ion Cascade Process and Physical State of the Implanted Solid)", S. T. Picraux, *Surface Engineering,* edited by R. Kossowski and S. C. Singhal, NATO ASI Series, 1984, pp. 3–29.

"New Viscosity Measurement: The Oscillating Magnetically Suspended Sphere", C. Leyh and R. Ritter, Rev. Sci. Instrum. 55(4), Apr. 1984, pp. 570–577 (p. 572 missing, pp. 570, 5.71, 573, 574, 576, 577 partly illegible).

"Simulation of Wear in Overhead Current Collection Systems", D. Klapas, Rev. Sci. Instrum. 56(9), Sep. 1985, pp. 1820–1828.

"Surface Modification of Industrial Components by Ion Implantation", P. Sioshanshi, Mater. Sci. Eng., 90, 1987, pp. 373–383.

"Optimixing Ion Implantation Conditions for Improving Wear, Fatigue, and Fretting Fatigue of Ti-6Al-4V", J. E. Elder, R. Thamburaj and P. C. Patnaik, Intl. Materials Rev., vol. 33, No. 6, 1988, pp. 289–313.

*The Art of Electronics,* Second Edition, Horowitz and Hill, Cambridge University Press, 1989, pp. 279–281.

"The Role of Oxide Particles in the Fretting Wear of Mild Steel", A. Iwabuchi, Wear, 151, 1991, pp. 301–311.

"Control of Fretting Friction and Wear of Roping Wire by Laser Surface Alloying and Physical Vapour Deposition Coatings", A. Batchelor, G. W. Stachowiak, and G. B. Stachowiak, Wear, 152, 1992, pp. 127–150 (p. 139 missing).

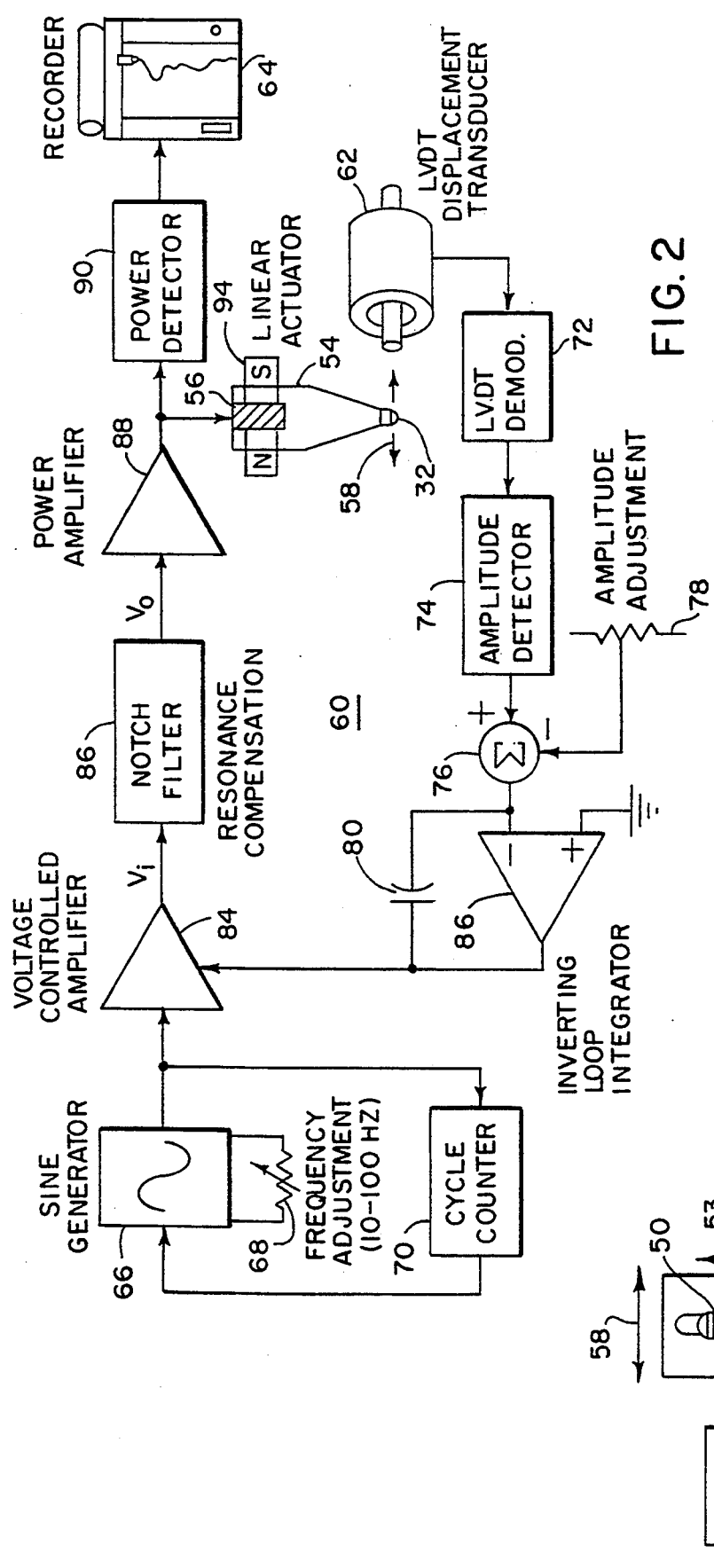
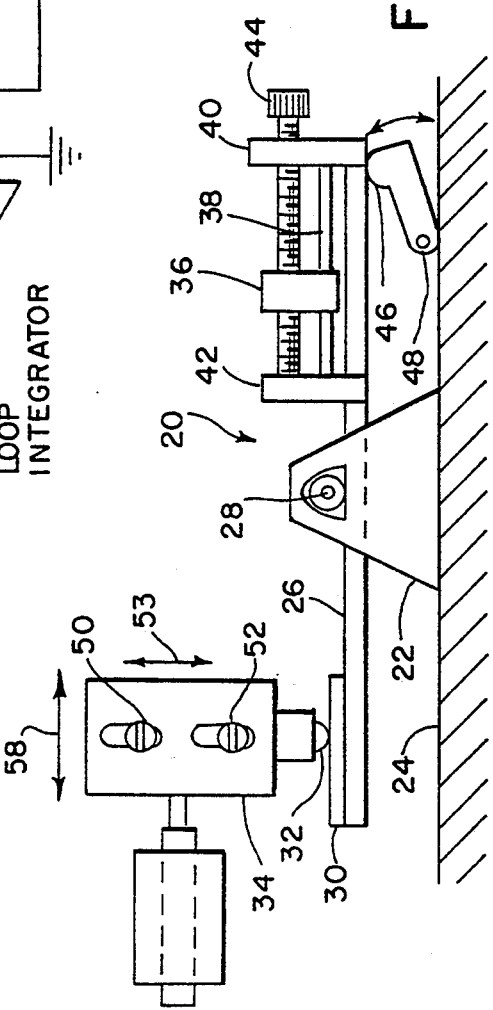

TESTING SYSTEM FOR DISSIPATIVE MECHANICAL PHENOMENA

BACKGROUND AND SUMMARY

The invention relates to systems for testing fretting wear and other dissipative mechanical phenomena such as viscosity measurement.

In fretting wear testing, knowledge of the amount of power, i.e. energy per unit time, consumed by frictional losses during the course of a wear test can provide insight into the dynamic processes that occur in fretting wear. This information is particularly useful in studies of surface-modified materials because the physical properties of such materials generally varies with the progression of wear. In viscosity measurement, current methods for measuring fluid viscosity are not suited for use in sensors. Advances in micro-machining techniques allow tiny mechanical structures to be manufactured using photolithographic techniques that are compatible with the manufacture of integrated electronic circuits. A piezo-electrically driven micro-actuator could be integrated with loop control, signal conditioning and temperature sensing circuitry, and an economical, self-contained viscometer sensor may be useful for process control and monitoring in the petroleum, biotechnology and food service industries.

Microscopic damage caused by fretting wear is of significant concern in many engineering applications. The present invention provides a versatile fretting wear testing apparatus and method which has been successfully applied to materials treated by plasma surface modifications, including nitrogen implantation, thin film alloy deposition, and diamond-like carbon film deposition.

Fretting refers to small amplitude, high frequency, oscillatory slip motion between two solid surfaces in contact, "Materials Evaluation Under Fretting Conditions" ASTM STP 780, June 1981, edited by S. R. Brown, Warminster, Pa 1981. The amplitude of the oscillations can vary from fractions of a micron to hundreds of microns, while typical frequencies range from tens to hundreds of Hertz. Fretting wear damage occurs in a number of applications, such as aircraft, automobiles, nuclear reactors, electrical contacts and surgical implants. Although fretting wear damage occurs in localized regions, it is often a precursor to catastrophic failure. Therefore, accurate assessment of fretting wear resistance of materials is of considerable technological and scientific significance.

The small slip amplitudes and high oscillating frequencies associated with fretting wear distinguish it from unidirectional wear. Phenomenologically, this leads to the accumulation of wear debris, products of chemical reaction, and limited heat transfer in the vicinity of the damaged region, G. Dearnaly in "Surface Engineering", edited by R. Kassowsky and S. Singhal (S'-Gravenhague, the Netherlands, Martinus Nyhoff, 1984) p. 125. Studies of the effect of slip amplitude on fretting wear have shown that surface damage can occur at amplitudes well under a micron, "Materials Evaluation Under Fretting Conditions", P. Kennedy, M. B. Peterson and L. Stallings, ASTM STP 780 June 1981, edited by S. R. Brown, Warminster, Pa. The identification of the upper limit of slip amplitude where the transition from fretting to unidirectional wear occurs is a subject of continued research. Systematic investigations of fretting wear damage up to slip amplitudes of 1,000 microns have shown that a dramatic increase in wear rate occurs in the range of 70 microns, suggesting that this might mark the upper limit for fretting wear: "Fretting Corrosion", R. B. Waterhouse, Pergamon Press, N.Y., 1972; N. Ohmae and T. Tsukizoe, Wear, 281, 1974. Other studies have noted a change in morphology and color of wear debris at about 100 microns, suggesting a change in wear mechanism from fretting to one that would be observed in a purely unidirectional wear situation: "Materials Evaluation Under Fretting Conditions", D. Kusner, C. Poon and D. W. Hoeppner, ASTM STP 780 June 1981, edited by S. R. Brown, Warminster, Pa; N. P. Suh, Wear, 44, 1, 1977; J. S. Halliday and W. Hirst, Proc. Roy. Soc. London, A-236, 411, 1956. Even with this systematic approach, a fundamental problem is that fretting wear depends on test conditions, environmental conditions, and the properties of the two contacting materials, H. Czichos and J. Molgaard, Wear, 44, 247, 1977.

The dependence of fretting wear on the oscillating frequency is strongly influenced by environmental conditions. With some materials, it has been noted that fretting wear rates decrease with increasing frequency up to about 30 Hz, H.H. Uhlig, J. App. Mech, 21, 401, 1954. This has been attributed to the relationship between the time for one fretting cycle and the kinetics of oxide film re-growth to a critical thickness where it can be wiped away and act as abrasive debris. The pivotal role of oxidation has been confirmed by high temperature studies where good agreement was reached between fretting wear rates and transition in temperature-dependent oxide growth mechanisms, P. L. Hurricks, Wear, 30, 189, 1974. Furthermore, it has been noted that fretting wear damage was independent of oscillating frequency when the testing was carried out in an inert atmosphere such as dry nitrogen, I. M. Feng and H.H. Uhlig, J. App. Mech, 21, 395, 1954.

The mechanism of material removal in a fretting wear process encompasses the effects of adhesion, abrasion and oxidation, J. E. Elder, R. Thamburaj and P. C. Patnaik, Intl. Materials Rev. 33, 289, 1988. It is believed that the wear process is initiated by localized adhesion of wear debris at surface asperities. The debris accumulates in the wear scar and is work hardened during subsequent cycles. Simultaneous oxidation of the freshly worn surface occurs, leading to the production of oxide particles. The work hardened debris and oxide particles lead to abrasive wear.

Previous designs for fretting wear testers have used a variety of mechanisms for generating the slip motion between the contacting surfaces: "Materials Evaluation Under Fretting Conditions", ASTM STP 780, June 1981, edited by S. R. Brown, Warminster, Pa 1981; J. Gensheimer, G. Friedrich, Wear, 17, 407, 1971. Most actuator designs fall into one of two general categories, mechanical or electromagnetic. Mechanical actuators rely on a rotating shaft in conjunction with a cam or out-of-balance weights to provide a reciprocal motion. The displacement amplitude is usually adjusted mechanically, with the frequency set by the rpm of the rotating shaft. Electromagnetic actuators can be controlled by electronic means and typically exhibit a broader frequency range than their mechanical counterparts. The present invention uses an electromagnetic actuator.

Most tribological studies depend on the observation of the effects of a controlled physical damage to the sample of interest. A purpose of the present fretting wear tester is to simulate the effects of small amplitude oscillatory wear. In one aspect, the present invention simulates the physical conditions that occur in real world situations where fretting wear is a relevant wear mechanism.

Analysis of a fretting wear scar can be accomplished using many of the same techniques common to other tribological tests, including optical and electron microscopy, profilometry and mass loss analysis. The present invention also provides for the in situ measurement of relative friction during the course of a wear process.

Fretting wear phenomena are difficult to study because of the many parameters that can play a significant role in a particular fretting wear process. Aside from the properties of the interacting materials themselves, the parameters that have been identified as being significant in fretting wear include: loading force; lubrication and/or corrosion at point of contact; amplitude of displacement; frequency of oscillation; and number of cycles. The present invention was designed to provide for the control of all of the above parameters in a repeatable manner.

In one aspect of the invention, an electro-mechanical actuator provides small amplitude, oscillatory slip motion between a stylus and a workpiece or fluid in a way that will result in dissipative interaction between the stylus and the workpiece material or fluid to be analyzed. A displacement transducer is used to monitor the amplitude of the stylus displacement providing the frictional oscillatory slip motion. A control loop 60 adjusts the actuator's excitation signal to keep the stylus displacement constant, i.e. constant amplitude slip motion. The amount of excitation power needed by the actuator to maintain a particular displacement, i.e. a constant amplitude slip motion, is related to the amount of dissipative loading caused by friction or viscosity and is described by the equation:

$$W_A = W_O + W_f$$

where $W_A$ is the power applied to the actuator, $W_O$ is the nominal power required to maintain the displacement without dissipative loading, and $W_f$ is the power consumed by the dissipative processes (friction or viscosity). If the actuator is driven at its resonant frequency, the system becomes particularly sensitive to dissipative loading because $W_O$ becomes very small. The power dissipated by frictional processes is proportional to the mechanical resistance to motion (friction or viscosity) according to the equation $$W_f \approx \frac{R(\omega A)^2}{2}$$

where R is a coefficient of friction, $\omega$ is the frequency of oscillatory slip motion, and A is the amplitude of the oscillator slip motion or displacement.

In another aspect of the invention, the amplitude and frequency of the slip motion can be independently varied to simulate a wide range of fretting conditions. The power needed by the electromagnetic actuator to maintain a constant displacement amplitude is sensitive to mechanical loading conditions. The amount of power supplied to the actuator is particularly sensitive to mechanical loading when the actuator is driven at its natural resonance, i.e. resonant frequency, as noted above. By providing a means to monitor the actuator excitation signal, a plot of the power expended during fretting wear by frictional processes is obtained.

BRIEF DESCRIPTION OF THE DRAWINGS

FIG. 1 is a schematic illustration of a fretting wear tester constructed in accordance with the invention.

FIG. 2 is a schematic circuit diagram illustrating the control loop for the present invention.

DETAILED DESCRIPTION

Figure 3:
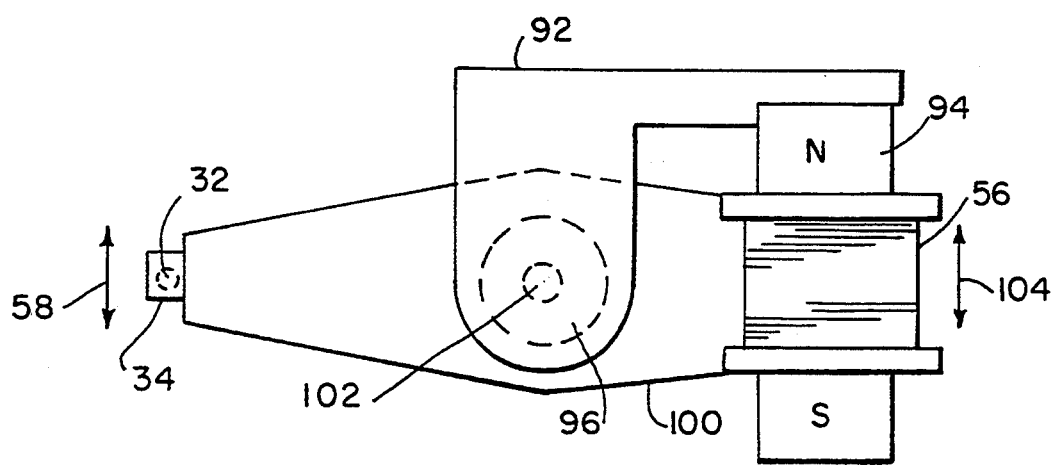
FIG. 3 is a top view of an electromagnetic actuator.

FIG. 1 shows a fretting wear tester 20 including a central support 22 resting on a base plate 24 and pivotally supporting a see-saw teeter-totter type lever arm 26 at fulcrum bearing 28. At the left end of lever 26 is a workpiece 30 or sample of material to be tested, and which is moved upwardly into contact with a stylus 32 attached to a stylus holder 34. On the right side of lever 26 is an adjustable sliding weight 36 guided along rod 38 between supports 40 and 42 and threaded on screw 44, such that as screw 44 turns, weight 36 moves left or right. This in turn balances the see-saw provided by lever 26 and adjusts the upward force of workpiece 30 against stylus 32. A cam 46 is pivotable about axis 48 and is driven by a motor (not shown) to rotate into engagement with the underside of lever 26 to provide a loading mechanism for gently bringing workpiece 30 into contact with stylus 32, to avoid initial impact pitting. Screws 50 and 52 enable adjustment of the height of the stylus holder as shown at 53.

The stylus is driven by an electromagnetic actuator 54, FIG. 2, preferably having a servo-coil 56 providing galvanometer-type servo-movement, which actuators are known in the art. The actuator moves the stylus left-right in FIGS. 1 and 2 as shown at 58. This provides frictional oscillatory slip motion between stylus 32 and workpiece 30, FIG. 1.

FIG. 2 shows a control loop 60 for maintaining constant amplitude displacement of stylus 32, i.e. constant amplitude oscillatory slip motion. The oscillatory slip motion is detected by a displacement transducer 62, such as a linear voltage displacement transducer, LVDT, also known as a linear variable differential transformer, provided by a Lucas Schaevitz Company Type 50HR LVDT. Displacement transducer 62 detects the amplitude of the slip motion. Control loop 60 responds to displacement transducer 62 and controls actuator 54 to provide constant amplitude slip motion including under changing frictional fretting wear conditions of workpiece 30 as the workpiece wears during the oscillatory slip motion of stylus 32 therealong. The control loop provides an excitation signal to the actuator, which excitation signal varies in response to displacement transducer 62. A strip chart recorder 64 provides a monitor monitoring the excitation signal to indicate changing power requirements of the actuator to maintain the noted constant amplitude slip motion under changing frictional fretting wear conditions of workpiece 30 as the latter wears. A frequency driver is provided by a sine wave generator 66, an Intersil ICL 8038, providing a frequency signal to the actuator to effect the oscillatory motion. The frequency is adjustable according to rheostat 68. The length of a test run is set according to a given number of cycles as counted by cycle counter 70.

The control loop includes an LVDT demodulator 72, provided by a Lucas Schaevitz Company SMS/GPM-109A signal conditioning module, supplying a conditioned signal to a precision rectifier acting as an amplitude detector 74 whose output is summed at summer 76 with a reference signal from potentiometer 78 providing a given adjustable reference affording amplitude adjustment. The output of the summer is filtered and smoothed by capacitor 80 and supplied to the inverting input of an operational amplifier 82 providing an inverting loop integrator, whose noninverting input is referenced to ground, and which inverting loop integrator is a standard configuration known in the art. The output of operational amplifier 82 controls the amplification of voltage controlled amplifier 84, which is an Analog Devices AD534, which in turn provides a controlled amplitude sine wave signal through notch filter 86, provided by a boot-strapped twin-tee notch filter, Horowitz and Hill, *The Art of Electronics*, Second Edition, Cambridge University Press, 1989, using National Semiconductor LM1458 op-amps, and through power amplifier 88, provided by a National Semiconductor LM1875 audio power amplifier, to actuator 54 to provide the excitation voltage for servo-coil 56. Notch filter 86 compensates for the loop's frequency dependent gain resulting from a preferably high Q mechanical resonance of the actuator. A high Q is preferred because less power is needed to maintain constant displacement amplitude at resonant frequency, to be described. The servo-coil excitation signal is also provided to recorder 64 through power detector 90, provided by an Analog Devices AD736 RMS to DC converter converting the excitation signal applied to the actuator into a DC signal usable by external data acquisition equipment.

In operation, if the amplitude of frictional oscillatory slip motion of stylus 32 decreases during the wearing of workpiece 30, then the output of transducer 62 decreases and the voltage at the inverting input of operational amplifier 82 decreases, and hence the output voltage from operational amplifier 82 increases, which in turn increases the amplification by amplifier 84 of the sine wave from generator 66, which in turn provides higher excitation voltage to servo-coil 56, which in turn increases the displacement amplitude of stylus 32 actuated by actuator 54. If the amplitude of frictional oscillatory slip motion of stylus 32 increases during the wearing of workpiece 30, then the output of transducer 62 increases and the voltage at the inverting input of operational amplifier 82 increases, and hence the output voltage from operational amplifier 82 decreases, which in turn decreases the amplification by amplifier 84 of the sine wave from generator 66, which in turn provides lower excitation voltage to servo-coil 56, which in turn decreases the displacement amplitude of stylus 32 actuated by actuator 54.

It is preferred that a high Q actuator be chosen, to provide high Q mechanical resonance, and that the actuator be operated at its natural resonant frequency, to effect the noted frictional oscillatory slip motion at such resonant frequency. The power needed by actuator 54 to maintain constant amplitude displacement is sensitive to mechanical loading conditions. The amount of power supplied to the actuator is particularly sensitive to dissipative mechanical loading when the actuator is driven at its natural resonance. The resonant frequency is determined by the mass of the actuator armature and the elasticity of the restoring spring. In operation, the resonant frequency is found by adjusting the frequency control at rheostat 68 until a minimum coil excitation signal is produced. It is preferred that the resonant frequency of the oscillatory motion be determined as if there were no friction between the stylus and the workpiece, e.g. before contact of the workpiece with the stylus, and then effecting the noted frictional oscillatory slip motion at such resonant frequency. This is accomplished by effecting the noted oscillatory motion with the actuator, detecting the amplitude of the oscillatory motion and producing an excitation signal in response thereto and providing the excitation signal to actuator 54 to control the amplitude of the oscillatory motion to maintain the amplitude constant, providing a frequency signal from generator 66 to actuator 54 to control the frequency of the oscillatory motion, and determining the resonant frequency by adjusting the frequency signal until a minimum excitation signal is produced.

Figure 5:
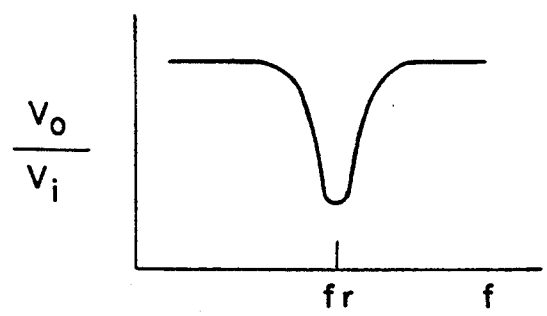
FIG. 5 is a graph showing notch filter attenuated response.

The control loop includes the noted notch filter 86 having an attenuated response at the noted resonant frequency. As shown in FIG. 5, notch filter 86 has an attenuated response at frequency $f_r$, i.e. the ratio of the output voltage $V_o$ to the input voltage $V_i$ is reduced at frequency $f_r$, which is preferably the resonant frequency of actuator 54. This compensates for the loop's frequency dependent gain, which dependence results from the high Q mechanical resonance of actuator 54. Significantly less power is needed to maintain constant displacement amplitude at the resonant frequency. The incorporation of notch filter 86 recognizes and accommodates this sensitivity. In one particular example, a resonant frequency of 40 Hz was chosen, and at a frequency different than resonant frequency, for example 45 Hz rather than 40 Hz, a coil excitation voltage of 1 volt is necessary to drive actuator 54 to produce 100 microns displacement; whereas at the resonant frequency of 40 Hz, a coil excitation voltage of only 10 millivolts is necessary to produce the noted 100 micron displacement. Notch filter 86 compensates such differential and enables faster response, greater range, and improved performance.

Figure 4:
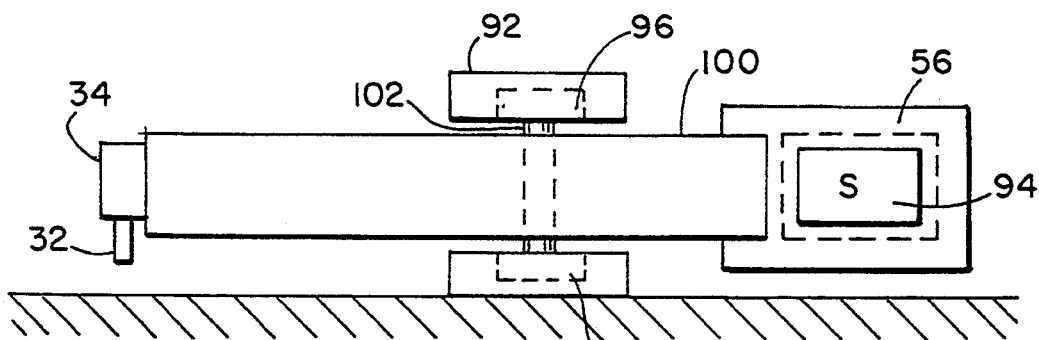
FIG. 4 is a side view of the actuator of FIG. 3.

FIGS. 3 and 4 show an actuator as noted above. A stationary frame 92 supports permanent magnet 94 and torsion bearings 96 and 98. Servo-coil 56 is fixedly mounted on armature 100. The armature is pivotally mounted between torsion bearings 96 and 98 on axle 102. Stylus holder 34 is mounted to the end of armature 100 opposite servo-coil 56. The noted excitation signal is provided to servo-coil 56 to cause the latter to move along stationary magnet 94 along direction 104, FIG. 3, which in turn causes armature 100 to pivot about its axis along axle 102 which in turn moves stylus holder 34 along direction 58. In the form shown in FIGS. 3 and 4, the high Q mechanical resonance of the actuator is determined by the mass of armature 100 and the elasticity of the restoring force provided by torsion bearings 96 and 98. In one embodiment, the torsion bearings are provided by Lucas Aerospace Corp. 6024-600 Lucas freeflex pivot bearings. In another embodiment, a leaf spring is additionally or alternatively connected between frame 92 and armature 100 for additional or alternative restoring force. A high Q mechanical resonance is preferred. The noted notch filter 86 compensates for variable loop gain versus frequency caused by such high Q mechanical resonance.

As noted above, in operation, the resonant frequency can be found by adjusting the frequency control at rheostat 68 until a minimum coil excitation signal is produced, which minimum coil excitation signal is sensed at recorder 64. At resonance, the amount of power needed by actuator 54 to maintain a given displacement is particularly sensitive to the dissipative loading caused by the interaction of stylus 32 and workpiece 30. Thus, by monitoring the power applied to servo-coil 56 of actuator 54, a measure of the power expended by frictional processes can be determined. In this way, the tribological properties of various materials undergoing fretting wear can be compared. This is particularly useful in testing surface modified materials, where information relating to changing wear mechanisms may be continuously obtained as wear proceeds through the modified surface layer. This signal can be plotted with a chart recorder 64 as shown, or with a computerized data acquisition system.

The effectiveness of the present apparatus and method for evaluating surface modified and coated materials has been demonstrated by the experiments noted below. For each of the three examples, a technique known as plasma source ion implantation, PSII, as disclosed in Conrad U.S. Pat. No. 4,764,394, was used to modify the surface of the test samples. In this technique, the items to be modified are placed directly in a plasma and pulse-biased to a high negative potential. A plasma sheath envelopes the item to be modified, accelerating ions normally towards all surfaces, thereby resulting in a uniform surface treatment. Depending on the composition of the plasma and the target bias level, a variety of surface modifications and coatings can be produced. This surface modification technique has been shown to have great potential for improving the wear resistance of engineering materials. The desire for a method to evaluate a variety of PSII treatments for the improvement of the fretting wear resistance of various materials was a motivation for the development of the present system.

In each of the following examples, the samples were polished with a 1 micron diamond paste and cleaned ultrasonically with acetone. A ruby ball was selected as the stylus material 32 because of its hardness and chemical inertness.

Ti-6Al-4V Alloy Implanted With Nitrogen

From the standpoint of biocompatibility, corrosion resistance and high strength-to-weight ratio, the Ti-6Al-4V alloy is an excellent material for surgical implants; however, it has inadequate wear resistance for such application. The implantation of nitrogen has been shown to improve the wear resistance of this alloy, P. Sioshanshi, Mater. Sci. Eng., 90, 273, 1987. A test sample of this alloy was implanted to a dose of $3 \times 10^{17}$ atoms/cm$^2$ with a target bias of 50 KeV. The implanted layer had a depth of about 1,500 angstroms.

Figure 6:
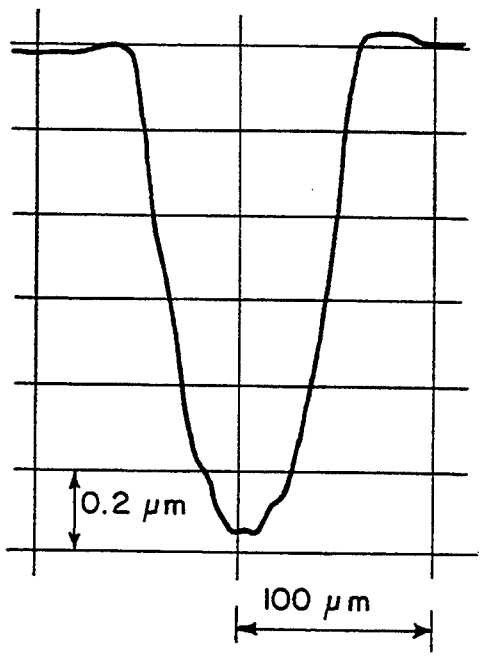
FIG. 6 is a graph showing a fretting wear profile along line 6—6 of FIG. 7.
Figure 7:
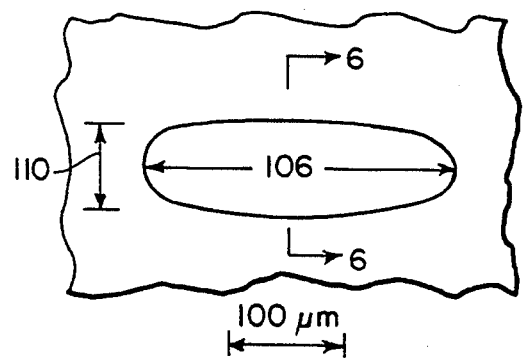
FIG. 7 shows a fretting wear scar.
Figure 8:
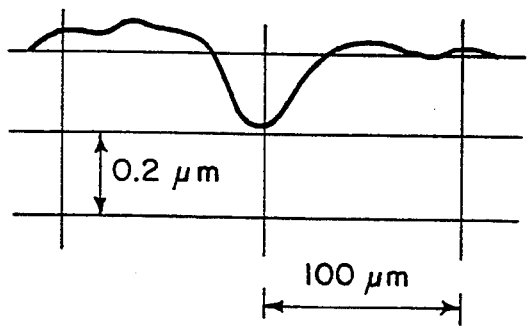
FIG. 8 is a graph showing a fretting wear profile along line 8—8 of FIG. 9.
Figure 9:
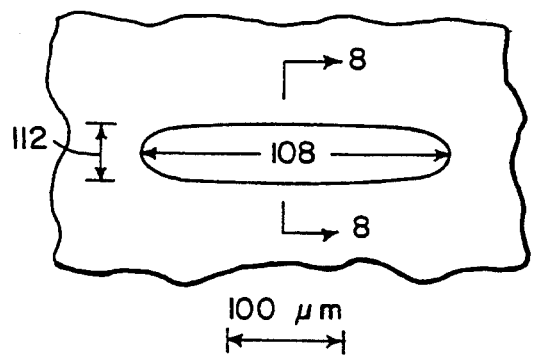
FIG. 9 shows a fretting wear scar.

FIG. 6 shows the depth profile, and FIG. 7 is a drawing of the optical micrograph of the fretting wear scar on an untreated sample taken with a Tencor Corp. alpha-step profilometer. FIG. 8 shows the depth profile, and FIG. 9 is a drawing of the optical micrograph of the fretting wear scar on a nitrogen-implanted sample. The fretting wear scar in the unimplanted sample, FIG. 6, is about six times deeper than in the implanted sample, FIG. 8. This shows significant improvement in fretting wear resistance after nitrogen implantation. It is speculated that the formation of hard titanium nitride particles at the surface are responsible for this improvement. Examination of the wear scars in FIGS. 7 and 9 indicates that nitrogen implantation changes the dominant wear mechanism from an adhesive to an abrasive oxidative mode. The equal scar lengths 106 and 108 in FIGS. 7 and 9 illustrate the good slip motion amplitude control of the present system. The unequal scar widths 110 and 112 stem from the different depths and the spherical geometry of the stylus.

Thin Film Deposition of Cr—Mo Alloy On Stainless Steel

Thin film surfaces that are resistant to the synergistic effects of fretting wear and corrosion have wide ranging industrial implications. A 1 micron Cr-12.5% Mo alloy film was deposited on stainless steel using the noted plasma source ion implantation process. The desired composition was achieved using two sputter cathodes with calibrated deposition rates. A krypton plasma was used to achieve complete mixing of the two alloying components.

Figure 10:
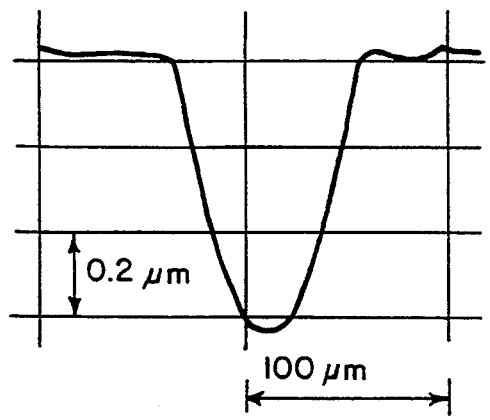
FIG. 10 is a graph showing a fretting wear profile along line 10—10 of FIG. 11.
Figure 11:
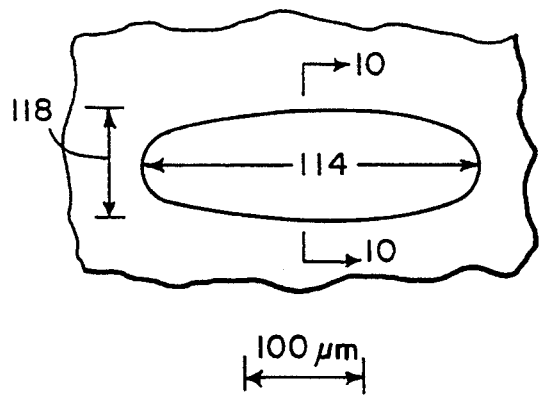
FIG. 11 shows a fretting wear scar.
Figure 12:
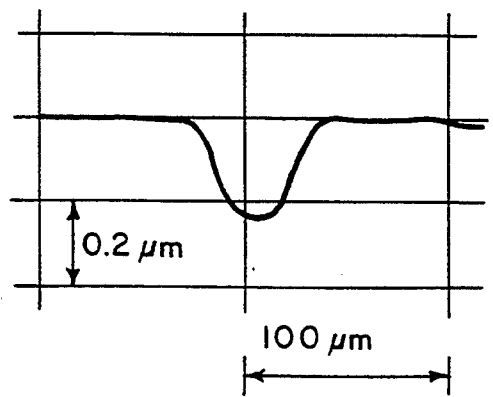
FIG. 12 is a graph showing a fretting wear profile along line 12—12 of FIG. 13.
Figure 13:
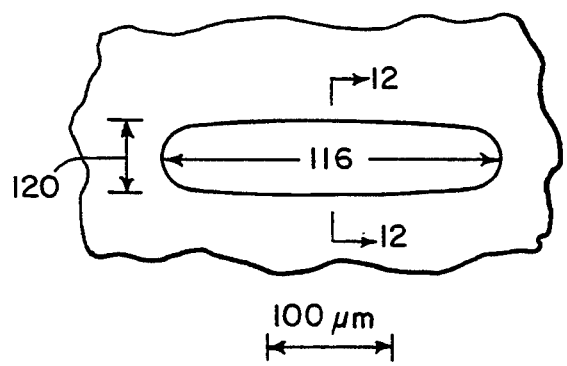
FIG. 13 shows a fretting wear scar.

FIG. 10 shows the fretting wear scar profile, and FIG. 11 is a drawing of the optical micrograph for the untreated stainless steel sample. FIG. 12 shows the fretting wear scar profile, and FIG. 13 is a drawing of the optical micrograph for the Cr—Mo deposited sample. The testing was carried out under identical conditions. A 0.1N sulfuric acid solution was used as a corrosive medium in both cases. The wear scar depth for the untreated sample, FIG. 10, is three times deeper than that for the treated sample, FIG. 12. The equal scar lengths 114 and 116 in FIGS. 11 and 13 illustrate the good slip motion amplitude control of the present system. The unequal scar widths 118 and 120 stem from the different depths and the spherical geometry of the stylus.

Diamond-like Carbon Film on Silicon Substrate

Diamond-like carbon (DLC) films are gaining popularity for tribological applications because of their hardness, low coefficient of friction and chemical inertness. A 0.15 micron DLC film was deposited on a Si substrate with a methane plasma using a target bias of 2 KeV.

Figure 14:
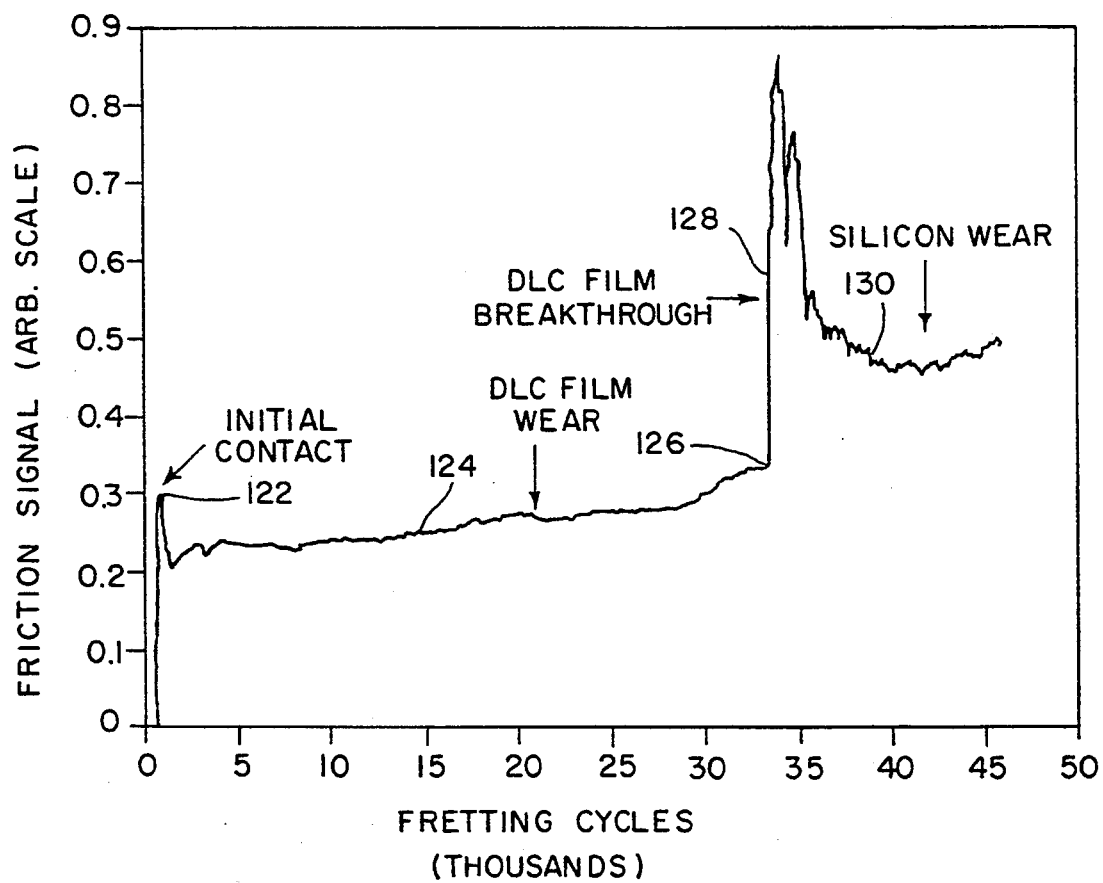
FIG. 14 is a graph of dissipative loading occurring during the progression of fretting wear.

FIG. 14 shows the friction signal, which is the servo-coil excitation voltage on an arbitrary scale, representing the resistance to motion of the stylus on the DLC film as the fretting wear progresses. The data was acquired while the system was operated in the resonant mode with a displacement amplitude of 100 microns. After the initiation of contact of the stylus and workpiece at 122, the friction signal stabilizes at 124. Breakthrough of the DLC film occurred at about 34,000 fretting cycles at 126, resulting in a sudden upsurge at 128 in the resistance to motion. This marked increase is indicative of the force needed to overcome the interfacial bonding between the film and the substrate. In the subsequent cycles at 130, the stylus is mainly in contact with the Si substrate where the friction signal is higher (at 130) than the DLC film (at 124).

The observation of trends in the friction signal provides in situ information regarding microstructural mechanisms at play during the fretting wear process. For example, the higher corrugation level at 130 after breakthrough possibly implies increased debris formation and interaction in the wear of Si as compared to DLC.

The invention provides a method for testing fretting wear including the steps of effecting frictional oscillatory slip motion between stylus 32 and workpiece 30 in contact, detecting the amplitude of the slip motion with linear voltage displacement transducer 62, controlling the slip motion with control loop 60 to provide constant amplitude slip motion, and monitoring at recorder 64 the power required to maintain constant amplitude slip motion under changing frictional fretting wear conditions of workpiece 30 as the workpiece wears during the noted oscillatory slip motion. The invention further provides a method for testing dissipative mechanical phenomena, such as viscosity measurement, including the steps of effecting oscillatory motion of a stylus 32 subject to resistance, detecting the amplitude of the oscillatory motion with transducer 62, controlling the oscillatory motion with control loop 60 to provide constant amplitude oscillatory motion, and monitoring at recorder 64 the power required to maintain constant amplitude oscillatory motion. The method involves detecting the amplitude of the oscillatory motion and modulating the excitation signal in response thereto to control the amplitude of the oscillatory motion to maintain such amplitude constant, and providing the excitation signal to the actuator at a frequency determined by the frequency signal, wherein the excitation signal has an amplitude component determined by the noted detecting of the amplitude of the oscillatory motion, and a frequency component determined by the frequency signal.

When driven at the frequency of mechanical resonance, the amount of power supplied to the actuator by the control loop to maintain constant amplitude displacement is particularly sensitive to dissipative loading. This can further be understood if it is remembered that actuator 54 requires the least amount of power when it is operated at its resonant frequency. If the actuator were ideal, with no losses due to friction in the bearings, etc., it would require zero power to maintain a particular displacement. Therefore, when at resonance, the power needed by the unloaded actuator is very small, namely on the same order as the power dissipated by frictional processes in the interaction between stylus 32 and workpiece 30. Furthermore, much of the power needed by the actuator goes towards compensating for these frictional losses to the workpiece. As noted above, the amount of excitation power needed by the actuator to maintain a particular displacement is related to the amount of dissipative loading caused by friction or viscosity and is described by the noted equation $W_A = W_O + W_f$, where $W_A$ is the power applied to the actuator, $W_O$ is the nominal power required to maintain the displacement without dissipative loading, and $W_f$ is the power consumed by dissipative processes (friction or viscosity). If the actuator is driven at its resonant frequency, the system becomes particularly sensitive to dissipative loading because $W_O$ becomes very small.

It is recognized that various equivalents, alternatives and modifications are possible within the scope of the appended claims.

I claim:

1. A method for testing fretting wear comprising effecting frictional oscillatory slip motion between a stylus and a workpiece in contact, detecting the amplitude of said slip motion, controlling said slip motion to provide constant amplitude slip motion, monitoring the power required to maintain said constant amplitude slip motion under changing frictional fretting wear conditions of said workpiece as said workpiece wears during said oscillatory slip motion.

2. The method according to claim 1 comprising determining a resonant frequency of said oscillatory motion, and effecting said frictional oscillatory slip motion at said resonant frequency.

3. The method according to claim 2 comprising:
   effecting said oscillatory motion with an actuator;
   detecting the amplitude of said oscillatory motion and producing an excitation signal in response thereto and providing said excitation signal to said actuator to control the amplitude of said oscillatory motion to maintain said amplitude constant;
   providing a frequency signal to said actuator to control the frequency of said oscillatory motion;
   determining said resonant frequency by adjusting said frequency signal until a minimum excitation signal is produced.

4. The method according to claim 3 wherein said frequency signal is a variable frequency sinusoidal signal, and wherein said resonant frequency is determined by adjusting the frequency of said sinusoidal signal until said minimum excitation signal is produced.

5. A fretting wear testing system comprising an actuator effecting frictional oscillatory slip motion between a stylus and a workpiece in contact, a displacement transducer detecting the amplitude of said slip motion, a control loop responsive to said displacement transducer and controlling said actuator to provide constant amplitude slip motion including under changing frictional fretting wear conditions of said workpiece as said workpiece wears during said oscillatory slip motion.

6. The system according to claim 5 wherein said control loop provides an excitation signal to said actuator, which excitation signal varies in response to said displacement transducer, and comprising a monitor monitoring said excitation signal to indicate changing power requirements of said actuator to maintain said constant amplitude slip motion under changing frictional fretting wear conditions of said workpiece as said workpiece wears during said oscillatory slip motion.

7. The system according to claim 5 comprising a frequency driver providing a frequency signal to said actuator to effect said oscillatory motion at a resonant frequency thereof.

8. The system according to claim 7 wherein said control loop provides an excitation signal in response to said amplitude of said slip motion detected by said displacement transducer, and provides said excitation signal to said actuator at a frequency determined by said frequency driver.

9. The system according to claim 8 wherein said control loop includes a notch filter having an attenuated response at said resonant frequency.

10. The system according to claim 8 wherein said control loop includes an operational amplifier having a first input responsive to the amplitude of said slip motion detected by said displacement transducer, and a second input referenced to a given reference, and having an output provided to a voltage controlled amplifier controlling amplification of said frequency signal and supplying same to said actuator.

* * * * *